United States Patent [19]

Dransfeld et al.

[11] Patent Number: 4,669,313
[45] Date of Patent: Jun. 2, 1987

[54] METHOD AND APPARATUS FOR LOCAL SELECTIVE DETECTION AND GENERATION OF POLAR STRUCTURE ALIGNMENTS IN MICROSCOPIC OBJECT AREAS

[75] Inventors: Klaus Dransfeld, Ermatingen, Switzerland; Knut Heitmann, Wetzlar, Fed. Rep. of Germany

[73] Assignee: Ernst Leitz Wetzlar GmbH, Wetzlar, Fed. Rep. of Germany

[21] Appl. No.: 733,189

[22] Filed: May 13, 1985

[30] Foreign Application Priority Data

May 14, 1984 [DE] Fed. Rep. of Germany ....... 3417864

[51] Int. Cl.⁴ .......................................... G01N 29/00
[52] U.S. Cl. .......................................... 73/606; 73/642; 369/110
[58] Field of Search ................... 73/606, 642; 369/110

[56] References Cited

U.S. PATENT DOCUMENTS

| 4,028,933 | 6/1977 | Lemons et al. | 73/606 |
| 4,072,411 | 2/1978 | Franks et al. | 350/356 |
| 4,543,486 | 9/1985 | Rose | 73/606 |
| 4,563,898 | 1/1986 | Kanda et al. | 73/606 |

*Primary Examiner*—Howard A. Birmiel
*Attorney, Agent, or Firm*—Schwartz, Jeffery, Schwaab, Mack, Blumenthal & Evans

[57] ABSTRACT

Polar structures in microscopic object areas, such as, for example, electric or magnetic dipoles, can be locally selectively detected with high resolution if either resonant ultrasonic waves are induced in the object area by a locally effective high-frequency field and are detected by means of a focused acoustic lens arrangement, or electric or magnetic high-frequency oscillations are induced in the object area by focused ultrasonic waves and are detected by an appropriate receiver. By comparing the phases and/or amplitudes of the induced and of the detected waves, these provide information on the existence and the direction of the dipoles. Existing dipole alignments can be made energetically unstable by a critical direct-current electric or magnetic field and locally selectively reversed by the focused ultrasonic beam.

23 Claims, 4 Drawing Figures

U.S. Patent    Jun. 2, 1987    4,669,313
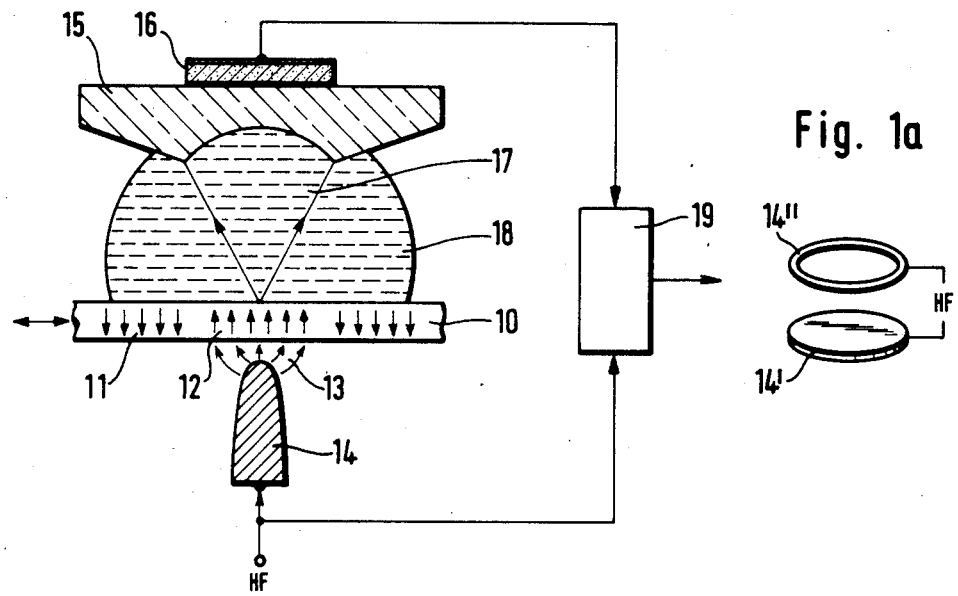
Fig. 1
Fig. 1a
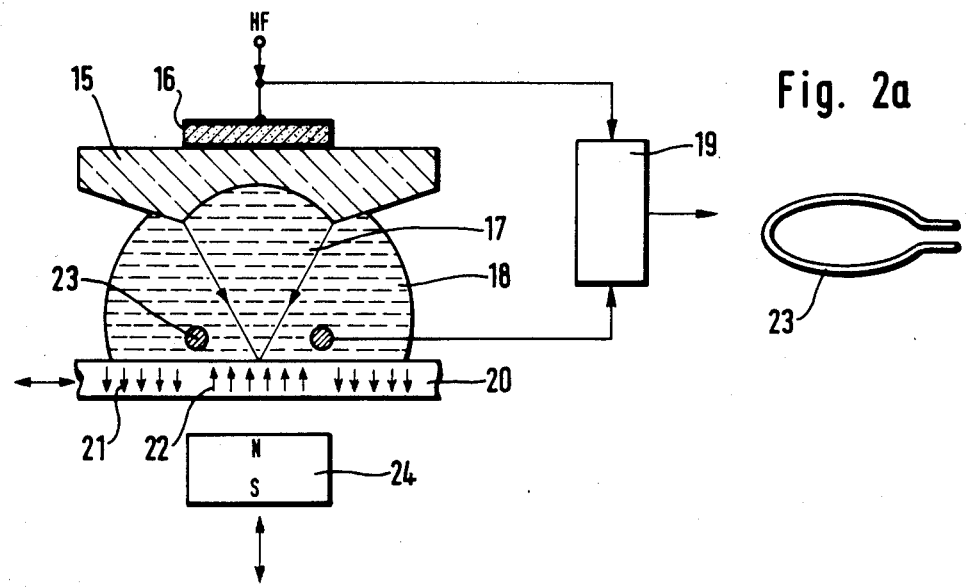
Fig. 2
Fig. 2a

METHOD AND APPARATUS FOR LOCAL SELECTIVE DETECTION AND GENERATION OF POLAR STRUCTURE ALIGNMENTS IN MICROSCOPIC OBJECT AREAS

BACKGROUND OF THE INVENTION

The present invention relates to a method and apparatus for local selective detection of polar structures in microscopic object areas and for local selective generation of polar structures with defined, stable alignment in microscopic areas of suitable objects.

It is known that both biological and crystalline or amorphous objects can have structures which are responsible for piezo-electric or magnetostrictive reactions of the objects. The basis for these effects is the existence of polar structures such as, in particular, electric or magnetic dipoles. In the biological field, for example, a cell membrane structure displays piezo-electric behavior. Certain plastic films can be excited into piezo-electric oscillations because of their ordered polymer structure. Magnetostrictive properties are predominantly utilized in systems generating ultrasonics (modulators). A purely magnetic alignment forms the basis of many data storage systems. In scientific research and, particularly, in the technology of data storage, a requirement exists to detect and, if possible, also to influence the existence and the distribution of the electric and magnetic dipoles in ever smaller object areas.

SUMMARY OF THE INVENTION

An object of the present invention is to provide a method and apparatus for selective detection and generation of polar structure alignments in order to achieve a resolution which is comparable or superior to that of methods of investigation by optical microscopy.

A further object of the present invention is to provide a method and apparatus in which the exciting radiation field differs from the detected radiation field so that they do not interfere with each other.

According to the present invention, the method for local selective detection of polar structures in microscopic object areas comprises directing a high-frequency radiation field having a frequency $\omega$ onto an object area using a locally effective transmitter to excite the object area and to induce in the object area resonant ultrasonic waves at the frequency $\omega$ or a harmonic of $\omega$. The induced ultrasonic waves are detected using an acoustic lens arrangement focused on the object area. The detected ultrasonic waves are converted into electric signals and the phase or amplitude of the exciting high-frequency field and the converted ultrasonic waves are compared with each other.

In accordance with other aspects, the invention also includes a method for local selective detection of polar structures in microscopic object areas, comprising directing a focused ultrasonic beam of frequency $\omega$ onto the microscopic object area using an acoustic lens arrangement to excite the object area and to induce in the irradiated object area high-frequency oscillations at the frequency $\omega$ or a harmonic of $\omega$. The induced oscillations are detected using a locally effective receiver and the phase or amplitude of exciting ultrasonic waves and the induced high-frequency field are compared with each other.

The radiation field may be an electric high-frequency field used for detecting electric polar structures.

The radiation field may also be a magnetic high-frequency field used for detecting magnetic polar structures.

Optionally, a direct current magnetic field may be superimposed on the high-frequency magnetic field for exciting magnetic resonance.

In accordance with further aspects, the invention includes a method for the local selective generation of polar structures with defined, stable alignment in microscopic areas of suitable objects, comprising subjecting the object area to a critical direct-current field to cause the polar alignment to become unstable and focusing an ultrasonic beam on the object area to bring the unstable polar structures into the required new stable alignment.

The invention also includes an apparatus for detecting polar structures contained in a microscopic object area. The apparatus comprises an acoustic lens system focused on the microscopic object area, and tuned to operate at a frequency or harmonics thereof and a radiation system directed onto the same object position and tuned to operate at the same frequency as said acoustic lens system, or harmonics thereof. One of the acoustic lens system and the radiation system transmits signals to the object area and the other receive corresponding signals from the object area induced by the transmitted signals. A comparator compares the phase or amplitude of the transmitted signals with said received signals.

The acoustic lens system and the radiation system may be located opposite each other on different sides of the object area, or the acoustic lens system and the radiation system may be arranged on the same side of the object area.

The radiation system may be a high-frequency electric field system, or a high-frequency magnetic field system.

An additional component may be directed onto the object area under examination for generating a direct-current radiation field of adjustable, critical intensity for producing polar structures with certain alignments.

Also, a permanent magnet may be provided having lines of flux of which are in alignment with those of the high-frequency magnetic field.

BRIEF DESCRIPTION OF THE DRAWINGS

In the text which follows, the subject-matter of the invention is explained in greater detail with the aid of the drawing. The figures show diagrammatically illustrative preferred embodiments of the invention. In the drawings:

FIG. 1 shows an arrangement for the detection of electric dipoles by ultrasonic detection, and FIG. 1a shows an alternative electrode arrangement, and FIG. 2 shows an arrangement for the detection of magnetic dipoles by HF detection, while FIG. 2a shows the conductor loop 23 thereof.

DETAILED DESCRIPTION OF THE PREFERRED EMBODIMENTS

The present invention is based on the finding that the dipoles in piezo-electric or magnetostrictive structures can be excited by an external high-frequency field into oscillations or precession movements which, in turn, generate ultrasonic waves having the frequency of excitation. These ultrasonic waves can be detected with the aid of an acoustic lens arrangement known from acoustical microscopy and can be converted into electric signals. Due to design parameters such as, for example, lens material and curvature of the lens surface, the acoustic lens arrangement defines a focal area which, with correspondingly high ultrasonic frequencies, can be smaller than in the case of optical objectives. Since the acoustic lens arrangement accepts only the ultrasonic waves originating in the focal area, it is only the acoustic lens arrangement which determines the size of the object area under examination. The apparatus for generating locally limited high-frequency fields can easily have a greater extent than this object area.

The same considerations also apply if the dipoles are excited into oscillations or precessions with the aid of a focused ultrasonic field and during this process generate high-frequency oscillations of the same frequency. Here, too, the extent of the ultrasonic focus defines the size of the object area under examination. To be able to receive the oscillations emanating from this object area, the receiver for the high-frequency oscillations needs only to be directed towards it.

The further advantage of the method according to the invention consists in that a physical difference exists in every case between the exciting radiation field and the detected radiation field so that the two radiation fields do not interfere with each other. This considerably facilitates separation of the signals. The frequency and the intensity both of the exciting high-frequency field and of an exciting ultrasonic wave field can be easily controlled, which makes it possible to obtain an optimum match to the object characteristics. A further possibility of matching results from the additional use of a direct-current magnetic field in the object area under examination with the aid of which field a resonant excitation of the magnetic dipoles can be achieved.

Since the generation of ultrasonics and the conversion of ultrasonics after the detection are carried out with the aid of piezo-electric transducers, electric signals are available both in the signal-excitation step and in the signal-detection step of the method, the mutual phase relationship and amplitude of which signals can be determined. In this process, the direction of polarization of the dipoles can be determined from a phase shift whilst the intensity of the detection signal permits conclusions to be drawn on the number and strength of the dipoles.

In FIG. 1, a piezo-electric film 10 of polyvinylidene fluoride (PVDF) is to be examined. A tape-shaped film of this material can be used, or example, as an audiotape on which the information items are stored in digital form. The individual bit zones 11, 12 are characterized by electric dipoles having different directions of polarization which are represented by the directions of the arrows in FIG. 1.

For the detection of the dipole groups, the PVDF tape is passed through a high-frequency electric field 13 which emanates from the tip of a needle-shaped transmitting electrode 14. The frequency of oscillation ω is, for example, in the GHz range. This arrangement then makes it possible to achieve, for example, a resolution of about 1 μm. The dipoles follow the exciting oscillation with a phase shift which is a function of their direction of polarization and, in turn, generate ultrasonic oscillations in synchronism with the exciting oscillation.

Opposite to the transmitting electrode, an acoustic lens arrangement is provided. This contains an ultrasonic objective 15 consisting of a sapphire rod into which a lens surface has been ground, and a piezo-electric transducer 16 which normally consists of a zinc oxide layer (ZnO) which is enclosed between two layers of gold acting as electrodes. The ultrasonic objective 15 is focused on the PVDF tape and collects only the ultrasonic waves entering the cone 17 of sound waves shown. A water drop 18 acts as a coupling medium for the transition of the ultrasonic beams from the PVDF type 10 to the ultrasonic objective 15. It can be seen that even with a very pointed transmitting electrode 14, the high-frequency field 13 irradiates a much larger area than is selectively covered by the ultrasonic objective 15. On the one hand, this makes it possible to carry out detailed examinations within the dipole groups 11, 12 and their boundary regions and, on the other hand, a much denser bit sequence could be selected which can still be resolved by the acoustic lens arrangement.

If, due to the object structure, the depths of penetration of the HF field and of the ultrasonic focus on the object are not adequate for the transmission arrangement shown in FIG. 1, it is also possible to arrange the transmitting electrode 14 on the same side as the ultrasonic objective 15. In this arrangement, the tip of the HF electrode must be directed towards the focal area of the ultrasonic objective. For generating a locally limited high-frequency field, an arrangement is also suitable which consists of a plate 14' and an opposite annular electrode 14''. The ring can be located on the same side as the acoustic lens arrangement, the ultrasonic focus being located in the inner area of the ring (FIG. 2a).

The exciting high-frequency oscillations and the electric signals produced at the piezo-electric transducer 16 are processed in a phase and/or amplitude measuring and comparing circuit 19 for further signal evaluation. If the PVDF tape 10 is moved relative to the measuring arrangement, the phase of the measuring signal will remain constant for as long as the dipole group 12 passes through the focal area of the ultrasonic objective. The amplitude of the measuring signal can change as a function of the density of the dipoles but becomes zero in the area between the dipole groups. As soon as, for example, dipole group 11 is detected by the ultrasonic objective, a phase jump occurs in the measuring signal.

In the illustrative embodiment of FIG. 2, the measuring task consists of detecting a vertical magnetization existing in a magnetic tape 20, and the direction of the magnetic dipoles 21, 22. The ultrasonic rays can be induced also in this case by a locally effective high-frequency magnetic field which is generated by a conductor loop 23 through which a high-frequency current flows. The frequency of oscillation ω is, for example, again in the GHz range. Due to the precession of the magnetic dipoles, ultrasonic waves are then generated which can be detected by the acoustic lens arrangement already described. The precession of the magnetic dipoles can be magnified by a superimposed direct-current magnetic field.

FIG. 2 shows the case where the acoustic lens arrangement 15, 16, excites the dipoles into a precession movement with the aid of the focused ultrasonic beam 17 and in this manner an alternating magnetic field of the same frequency is generated which is detected with the aid of the current loop 23. The excitation of the dipoles is here limited to a much smaller area than is utilized for detecting the induced magnetic field. For the rest, the same considerations apply as for the arrangement of FIG. 1. The arrangement can be advantageously supplemented by the arrangement of an additional direct-current magnetic field 24. In this field, the dipoles in the magnetic tape 20 can be resonantly excited with appropriate choice of the ultrasonic frequency. The resonant frequency of the dipoles 22 (spin up) is clearly different from that of the dipoles 21 (spin down) so that a comparison of the amplitudes provides another criterion for the detection of the dipole directions.

With a suitable choice of the field strength of the permanent magnets 24 (for example a samarium magnet), the possibility also exists of using the arrangement described for generating certain magnetic dipole alignments. For the magneto-optical storage of information, materials are known which can be magnetized at right angles to the surface and in which this direction of premagnetization can be locally reversed by optical radiation. As an example, thin films of an amorphous ferromagnetic alloy of gadolinium acid iron (GdFe) are mentioned. If, in the arrangement of FIG. 2, such a film is used as the magnetic tape 20, the premagnetized dipoles can be energetically raised by the constant field of the magnet 24 to such an extent that the magnetic compensation temperature of the alloy (Curie point) is nearly reached. Using a pulse-modulated ultrasonic beam, the energy of the dipoles can then be raised above the Curie point so that the direction of polarization reverses in synchronism with the modulation. With a moving recording medium, the storage densities that can be achieved in this manner are at least as great as with optical recording techniques. If ultrasonic frequencies of several GHz are used, the storage density could even be increased because of the reduced focal extent. However, it is essential that the information written in can also be read out again with the same resolution by the same arrangement after the direct-current magnetic field has been switched off.

What is claimed is:

1. A method for local selective detection of polar structures in microscopic object areas, comprising:
   directing a high-frequency radiation field having a frequency $\omega$ onto an object area using a locally effective transmitter to excite the object area and to induce in the object area resonant ultrasonic waves at the frequency $\omega$ or a harmonic of $\omega$;
   detecting the induced ultrasonic waves using an acoustic lens arrangement focused on the object area;
   converting the detected ultrasonic waves into electric signals; and
   comparing the exciting high-frequency field and the converted ultrasonic waves with each other.

2. A method as claimed in claim 1, wherein said radiation field is an electric high-frequency field used for detecting electric polar structures.

3. A method as claimed in claim 1, wherein said radiation field is a magnetic high-frequency field used for detecting magnetic polar structures.

4. A method as claimed in claim 3, including the step of superimposing a direct-current magnetic field on the high-frequency magnetic field for exciting magnetic resonance.

5. A method as claimed in claim 1, wherein said comparing step comprises comparing the phases of said exciting field and said converted waves.

6. A method as claimed in claim 1, wherein said comparing step comprises comparing the amplitudes of said exciting field and said converted waves.

7. A method for local selective detection of polar structures in microscopic object areas, comprising:
   directing a focused ultrasonic beam of frequency $\omega$ onto the microscopic object area using an acoustic lens arrangement to excite the object area and to induce in the irradiated object area high-frequency oscillations at the frequency $\omega$ or a harmonic of $\omega$;
   detecting the induced oscillations using a locally effective receiver; and
   comparing the exciting ultrasonic waves and the induced high-frequency field with each other.

8. A method as claimed in claim 7, wherein said radiation field is an electric high-frequency field used for detecting electric polar structures.

9. A method as claimed in claim 7, wherein said radiation field is a magnetic high-frequency field used for detecting magnetic polar structures.

10. A method as claimed in claim 9, including the step of superimposing a direct-current magnetic field on the high-frequency magnetic field for exciting magnetic resonance.

11. A method as claimed in claim 7, wherein said comparing step comprises comparing the phases of said exciting field and said converted waves.

12. A method as claimed in claim 7, wherein said comparing step comprises comparing the amplitudes of said exciting field and said converted waves.

13. A method for the local selective generation of polar structures with defined, stable alignment in microscopic areas of suitable objects, comprising:
   subjecting the object area to a critical direct-current field to cause the polar alignment to become unstable; and
   focusing an ultrasonic beam on the object area to bring the unstable polar structures into the required new stable alignment.

14. An apparatus for detecting polar structures contained in a microscopic object area, comprising:
   an acoustic lens system focused on the microscopic object area, and tuned to operate at a frequency $\omega$ or harmonics thereof; and
   a radiation system directed onto the same object area and tuned to operate at the same frequency as said acoustic lens system, or harmonics thereof;
   wherein one of said acoustic lens system and said radiation system transmits signals to said object area to excite said object area and the other receives corresponding signals from said object area induced by said transmitted signals; and
   a comparator for comparing said transmitted signals with said received signals.

15. An apparatus as claimed in claim 14, wherein the acoustic lens system and the radiation system area located opposite each other on different sides of the object area.

16. An apparatus as claimed in claim 14, wherein the acoustic lens system and the radiation system are arranged on the same side of the object area.

17. An apparatus as claimed in claim 14, wherein the radiation system is a high-frequency electric field system.

18. An apparatus as claimed in claim 17, including additional means directed onto the object area under examination for generating a direct-current radiation field of adjustable, critical intensity for producing polar structures with certain alignments.

19. An apparatus as claimed in claim 18, wherein the additional means is switchable.

20. An apparatus as claimed in claim 14, wherein the radiation system is a high-frequency magnetic field system.

21. An apparatus as claimed in claim 20, including a permanent magnet having lines of flux of which are in alignment with those of the high-frequency magnetic field.

22. An apparatus as claimed in claim 20, including additional means directed onto the object area under examination for generating a direct-current radiation field of adjustable, critical intensity for producing polar structures with certain alignments.

23. An apparatus as claimed in claim 22, wherein the additional means is switchable.

* * * * *